US008234800B2

United States Patent
Buder et al.

(10) Patent No.: US 8,234,800 B2
(45) Date of Patent: Aug. 7, 2012

(54) SHOE, PARTICULARLY SPORTS SHOE

(75) Inventors: Jens Buder, Chemnitz (DE); Stephan Odenwald, Chemnitz (DE)

(73) Assignee: Puma SE, Herzogenaurach (DE)

( * ) Notice: Subject to any disclaimer, the term of this patent is extended or adjusted under 35 U.S.C. 154(b) by 0 days.

(21) Appl. No.: 13/321,237

(22) PCT Filed: May 7, 2010

(86) PCT No.: PCT/EP2010/002810
§ 371 (c)(1),
(2), (4) Date: Jan. 13, 2012

(87) PCT Pub. No.: WO2010/133300
PCT Pub. Date: Nov. 25, 2010

(65) Prior Publication Data
US 2012/0102784 A1    May 3, 2012

(30) Foreign Application Priority Data

May 19, 2009    (DE) .................... 20 2009 007 220 U

(51) Int. Cl.
*A43B 7/24* (2006.01)
*A43B 21/26* (2006.01)
*A43B 21/433* (2006.01)
(52) U.S. Cl. .............. 36/144; 36/143; 36/25 R
(58) Field of Classification Search ............ 36/142–144, 36/29, 35 B, 25 R
See application file for complete search history.

(56) References Cited

U.S. PATENT DOCUMENTS

| 5,813,142 | A | 9/1998 | Demon | |
|---|---|---|---|---|
| 6,430,843 | B1* | 8/2002 | Potter et al. | 36/29 |
| 6,457,262 | B1* | 10/2002 | Swigart | 36/29 |
| 6,892,477 | B2* | 5/2005 | Potter et al. | 36/29 |
| 7,707,742 | B2* | 5/2010 | Ellis, III | 36/25 R |
| 7,793,430 | B2* | 9/2010 | Ellis | 36/25 R |
| 2002/0053146 | A1* | 5/2002 | Swigart | 36/29 |
| 2003/0009913 | A1* | 1/2003 | Potter et al. | 36/29 |
| 2003/0056401 | A1* | 3/2003 | Kwon | 36/127 |
| 2005/0132617 | A1* | 6/2005 | Potter et al. | 36/132 |

(Continued)

FOREIGN PATENT DOCUMENTS

DE    20 2005 007 949 U1    8/2005
(Continued)

*Primary Examiner* — Marie Patterson
(74) *Attorney, Agent, or Firm* — Lucas & Mercanti, LLP

(57) ABSTRACT

The invention relates to a shoe, especially to a sports shoe, comprising a shoe upper (1) and a sole (2), wherein at least one actuator (3) is arranged in the sole (2), by means of which a region of the contact surface (4) for the foot of the wearer of the shoe can be affected with regard to the geometry of the contact surface (4) at least in a defined length range ($B_L$) and/or width range ($B_B$) of the sole (2) relatively to the position of the contact surface (5) of the sole (2) on the ground. In order to make the required actuating motion of the actuator using little energy, the invention proposes that the actuator (3) comprises a support element (6) supporting the foot of the wearer, which is pivotally disposed relatively to a base part (7) around an axis (A), wherein at least one hydraulic chamber (8, 9) having a variable volume is arranged on each side of the axis (A) between the support element (6) and the base part (7), which are completely filled with a substantially incompressible medium, wherein the at least two hydraulic chambers (8, 9) are fluidically connected to each other by means of a conduit (10) in which a switchable valve (11) is disposed.

16 Claims, 4 Drawing Sheets

U.S. PATENT DOCUMENTS

Figure 1:
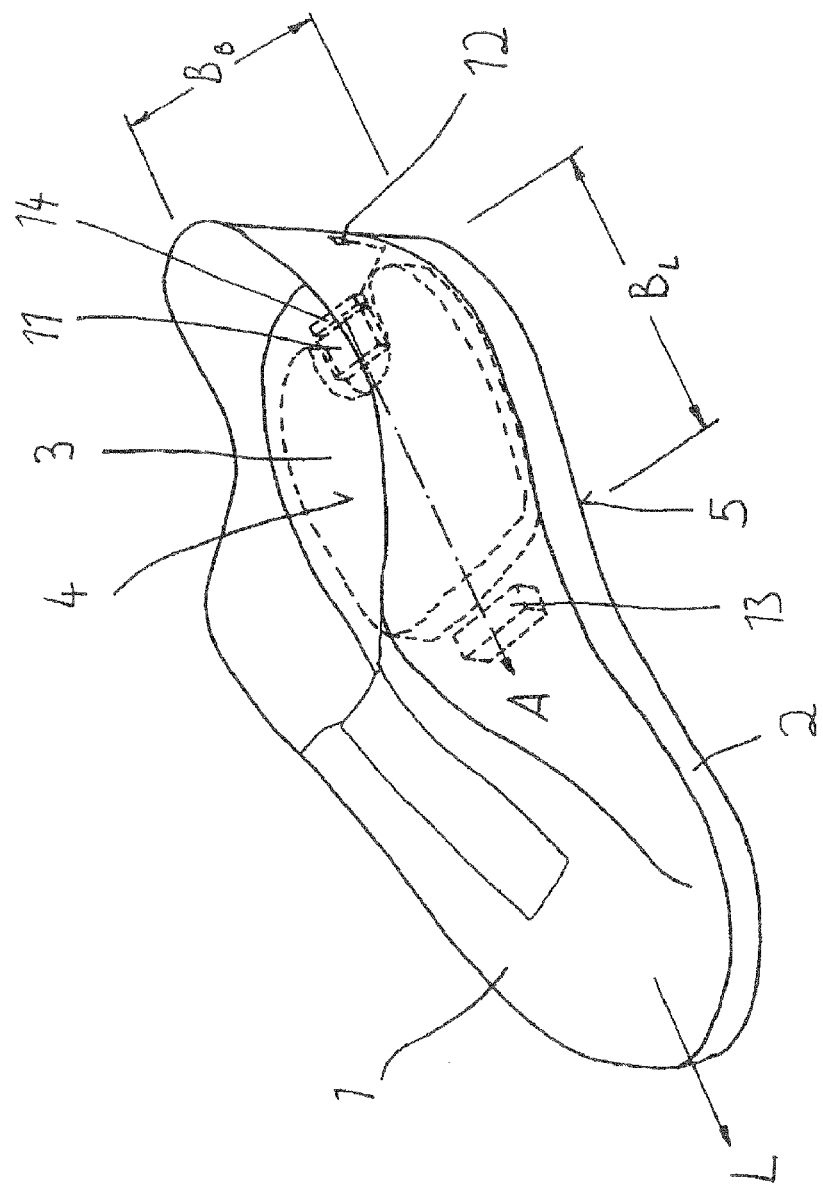

2007/0006489 A1   1/2007   Case, Jr.

FOREIGN PATENT DOCUMENTS

| | | |
|---|---|---|
| DE | 10 2004 063 876 A1 | 11/2005 |
| DE | 20 2007 018 163 U1 | 5/2009 |
| FR | 2 898 017 A1 | 9/2007 |
| WO | 01/78539 A2 | 10/2001 |
| WO | 2009/027941 A2 | 3/2009 |

* cited by examiner

SHOE, PARTICULARLY SPORTS SHOE

This application is a continuation application of PCT/EP2010/002810 filed May 7, 2010, which in turn claims the priority DE 20 2009 007 220.7, filed May 19, 2009, the priority of these applications is hereby claimed and these applications are incorporated by reference herein.

The invention relates to a shoe, especially to a sports shoe, comprising a shoe upper and a sole, wherein at least one actuator is arranged in the sole, by means of which a region of the contact surface for the foot of the wearer of the shoe can be affected with regard to the geometry of the contact surface at least in a defined length range and/or width range of the sole relatively to the position of the contact surface of the sole on the ground.

A shoe of this kind is known for example from DE 20 2007 018 163 U1. Here, it is provided to equip a sports shoe with a system by which the pronation and supination behaviour respectively of the shoe can be influenced actively.

The pronation is a rotation of the foot around an axis of the lower ankle joint by which the outer edge of the foot is lifted and the inner edge of the foot is lowered. The pronation is also called inward rotation or inward canting. The normal pronation is a natural damping mechanism and a natural movement inwardly when the foot touches the ground. However, the edge of the foot flexes intense inwardly during the so-called over-pronation and thus stresses the ligaments, sinews, and joints. This over-pronation can have different reasons, e.g. a malposition of the foot, overweight, or intense fatigue. Also, over-pronation occurs casually in the case of running beginners because the support apparatus of the foot is not yet trained sufficiently. Often, an intense wear can then be found in the medial region of the shoes.

The mechanism which is directed against the pronation (also called supination) occurs less often during running. During supination the forces act in the contrarious direction. Often, this can be observed when running shoes have a higher wear in the lateral region (thus at the outer side).

Accordingly, it is aimed in modern sports shoes to carry out an active influence of the pronation which goes beyond the known pronation footholds which are integrated into the sole, what is possible by a system as described in the mentioned document.

For doing so actuation systems are provided in the mentioned DE 20 2007 018 163 U1 by which the height of an actuation element in vertical direction can by varied in such a manner that the contact surface of the sole on which the foot of the wearer rests is changed relatively to the contact surface of the sole on the ground. Because the actuation element is laterally offset from the longitudinal axis of the shoe in the sole a tilting of the contact surface for the foot can be carried out which is controlled in such a manner that a desired pronation and supination behaviour respectively is reached.

For adjusting of the effective vertical height of the actuation element the same is supplied with energy by an energy source (battery) which is housed in the shoe accordingly. Namely, the actuation element has an actuator by which the adjustment can be carried out. Also, the energy supply is necessary to supply a control device and closed-loop control device respectively with energy which transforms a signal which is detected by a sensor into a respective actuation signal for the actuation element.

It is desirable in this connection to design the energy source, i.e. the battery, as small as possible to save weight.

Thus, it is the object of the invention to further develop a shoe, especially a sports shoe, of the kind mentioned at the beginning in such a manner that it becomes possible to carry out the required actuation movement of a generic actuator with a small demand of energy, wherein however an effective influence of the pronation and supination behaviour respectively is ensured.

The solution of this object by the invention is characterized in that the actuator comprises a support element supporting the foot of the wearer, which is pivotally disposed relatively to a base part around an axis, wherein at least one hydraulic chamber having a variable volume is arranged on each side of the axis between the support element and the base part, which are completely filled with a substantially incompressible medium, wherein the at least two hydraulic chambers are fluidically connected to each other by means of a conduit in which a switchable valve is disposed.

Thereby, the actuator is preferably arranged in the shoe in such a manner that the axis coincides with the longitudinal axis of the shoe. But this is not mandatory. The axis can e.g. also be arranged parallel beside the longitudinal axis of the shoe.

Thereby, the actuator is preferably arranged in the rear foot region of the sole. Advantageously, it is arranged in the rearmost third of the extension of the sole in the direction of the longitudinal axis of the shoe. With respect to the extension of the actuator in the direction of the width it has to be stated that the actuator extends preferably along at least 80% of the width of the sole; but also a smaller value can be realized.

The support element as well as the base part are formed preferably as a panel. But this is not mandatory. Furthermore, it can be provided that a bar is arranged between the base part and the support element extending in the direction of the axis which acts as a tilting joint.

The hydraulic chambers comprise preferably an elongated chamber part which extends offset to the axis in the direction of the axis. The hydraulic chambers are mostly filled with hydraulic oil; but each incompressible fluid is suitable.

The actuator is devoid of any actuating element provided by an energy source. The regulation of the actuator takes place exclusively by the energy which is brought in by the body mass of the wearer of the shoe from the foot of the wearer onto the actuator.

Furthermore, the shoe has preferably a system which comprises the at least one actuator for automatically influencing the pronation of the foot of the wearer of the shoe. This system for automatically influencing the pronation comprises mostly a suitable sensor for detecting of a parameter which is relevant for the pronation, an energy source and a control device and closed-loop control device respectively. The valve can be actuated by the control device and closed-loop control device respectively.

Preferably, the valve is a proportional valve; but also other kinds of valves are thinkable. Furthermore, it can be a 2-way valve; however also other way valves are possible.

By the proposed solution it becomes possible to influence the geometry of the sole of the shoe effectively so that the pronation behaviour of the shoe can be specifically influenced. Thereby, especially the angle position of the contact surface of the sole for the foot relatively to the contact surface of the shoe on the ground is changed in such a manner that a desired pronation behaviour is obtained. Thus, the contact surface of the sole for the foot of the wearer is tilted—relatively to the ground—in such a manner that the pronation does not exceed a desired degree. It is an advantage of the described solution that this becomes possible without any energy input into the actuator, disregarding the energy which is necessary to actuate the valves which is however minor.

Accordingly, the pronation behaviour can be effectively influenced with a very small energy source (battery) which is required only for the control device and closed-loop control device respectively and the valve actuation. Rather, the energy for the adjustment of the actuator is attained from the energy, which is delivered by the wearer of the shoe onto the actuator during normal running.

It should be emphasized that the spring and damping behaviour is not influenced by the use of a substantial incompressible fluid in the hydraulic chambers which is not intended anyway. Merely the adjustment of the actuator is carried out by the proposed concept; the actuator itself is substantially rigid and makes no contribution to the springiness and the damping of the sole of the shoe.

In the drawing an embodiment of the invention is depicted.

Figure 2:
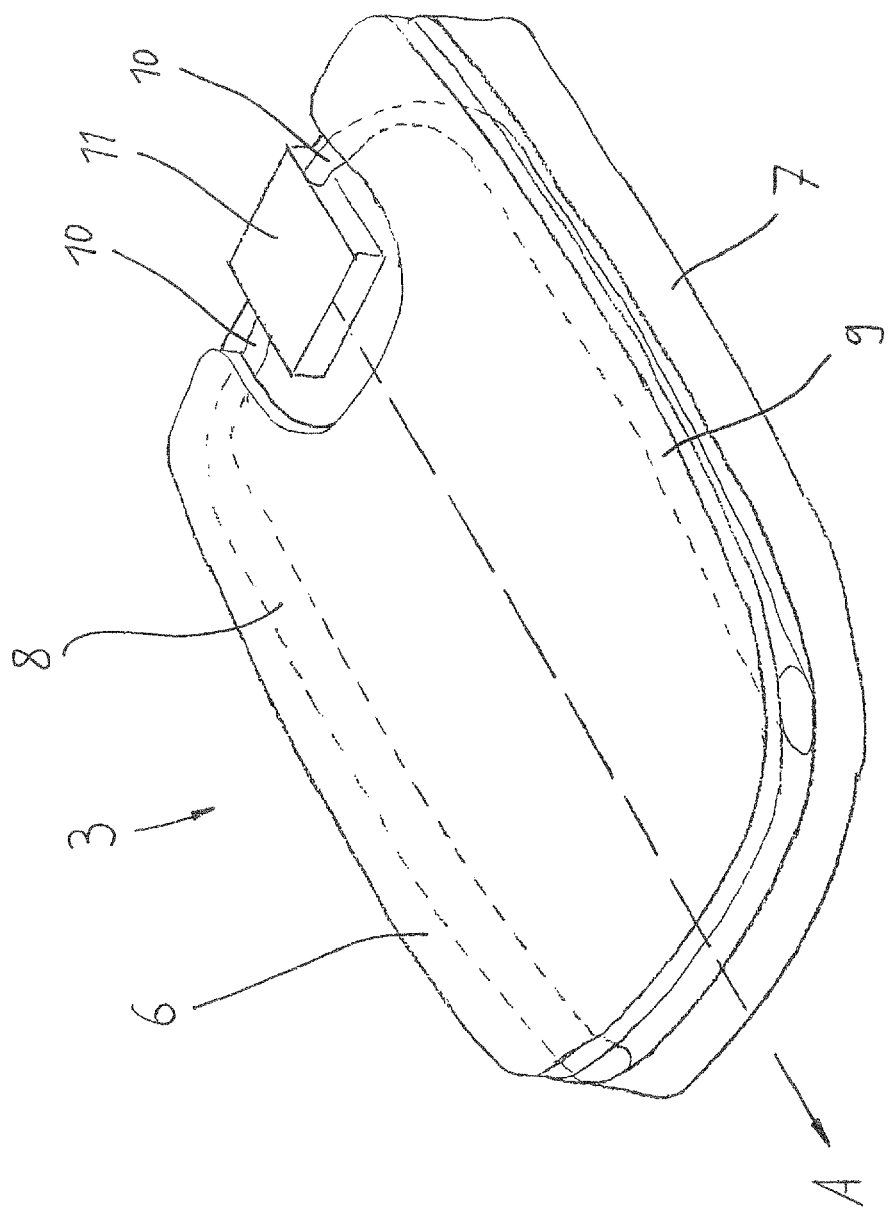
Figure 3:
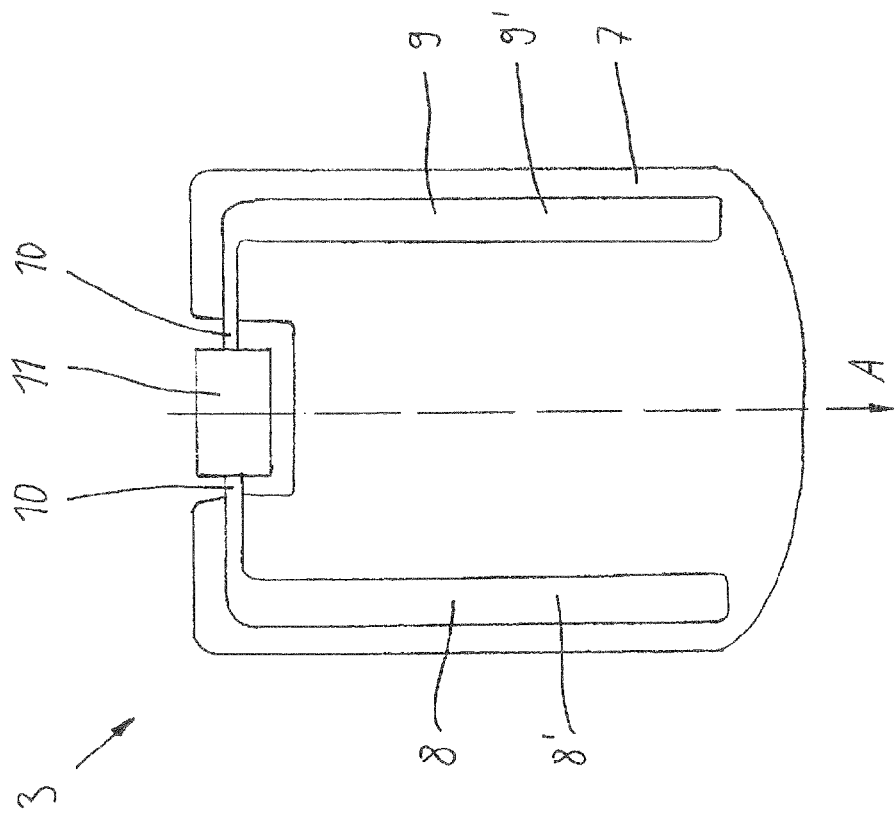
Figure 4C:
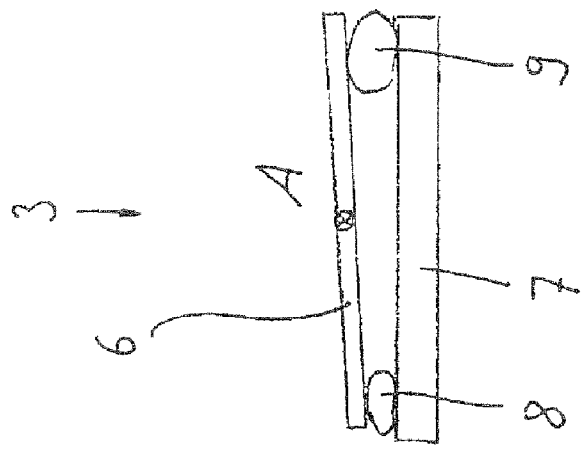
Figure 4B:
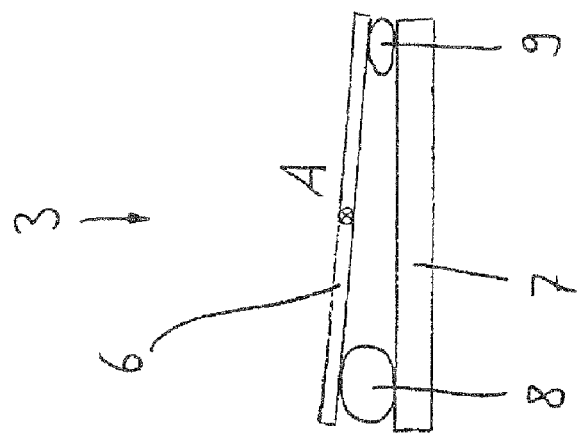
Figure 4A:
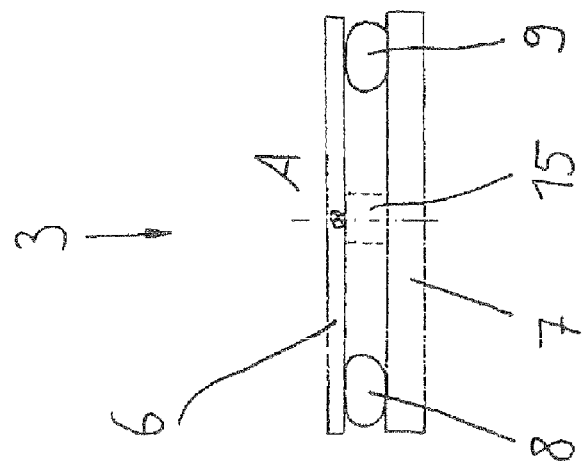

FIG. 1 shows a sports shoe in a perspective view,

FIG. 2 shows an actuator in a perspective view which is housed in the sole of the sports shoe, FIG. 3 shows the actuator in a top plan view, wherein a panel-shaped support element being arranged in the upper region is removed, FIG. 4a shows schematically the actuator in the front view, seen in the direction of a tilting axis A, wherein no pivoting of the support element relatively to a base part exists, FIG. 4b shows the actuator in the front view according to FIG. 4a, wherein a pivoting of the support element relatively to the base part in a first pivoting direction exists, and FIG. 4c shows the actuator in the view according to FIG. 4a, wherein a pivoting of the support elements relatively to the base part in a second pivoting direction exists.

In FIG. 1 a sports shoe is shown which consists substantially of a shoe upper 1 and a sole 2 in known manner. The shoe has a longitudinal axis L.

The shoe is equipped with a system by which the pronation behaviour of the shoe and of the foot of the wearer respectively can be influenced. This system comprises substantially a sensor 12 by which a parameter can be detected which is relevant for the pronation behaviour, for example the rotational speed or the rotation angle of the shoe around a defined axis. Furthermore, the system comprises a control device and closed-loop control device respectively 14 which receives the measuring values detected by the sensor 12. Furthermore, the system comprises an actuator 3 which is controlled by the control device and closed-loop control device respectively 14. The actuator 3 is described in more detail subsequently. It is important that it has no own actuator element (e.g. motor) by which is could carry out an adjustment movement. However, for the energy supply of the control device and closed-loop control device respectively 14 an energy source 13 being a battery is provided. It can be designed very small as it must deliver only little energy. The control device and closed-loop control device respectively 14 can also be placed at another location as it is shown by FIG. 1.

The actuator 3 is arranged in the rear foot or heel region of the shoe. In the embodiment it extends along about the rearmost third of the sole 2 measured in the direction of the longitudinal axis L. The possible dimensions of the actuator 3 are indicated with $B_L$ for the length range and with $B_B$ for the width range.

During activating of the actuator 3—only during running and during the contact phase with the ground—a contact surface 4 for the foot of the wearer of the shoe tilts around an axis A relatively to the contact surface 5 of the sole 2 on the ground. The contact surface 4 for the foot is the surface of the sole on which the foot of the wearer of the shoe rests.

The tilting or pivoting axis A of the actuator 3 is presently identical with the longitudinal axis L of the shoe. But this is not mandatory.

Details of the design of the actuator 3 can be seen from FIG. 2 and FIG. 3. The actuator 3 has a base part 7 being arranged in the lower region which can be fixed in the sole 2, for example it can be glued in a respective recess in the sole 2. Furthermore, the actuator 2 has a support element 6 being arranged in the upper region on which the foot of the wearer rests—indirectly separated by a not depicted insole and where required by a midsole.

Two hydraulic chambers 8 and 9 are arranged between the base part 7 and the support element 6 as can be seen from the synopsis of the FIGS. 2 and 3. The hydraulic chambers 8, 9 are filled e.g. with hydraulic oil or another substantial incompressible liquid. As the base part 7 as well as the support element 6 consist preferably of a substantial rigid material (e.g. of plastic material like polyamide or of light metal) the whole actuator 3 forms a substantial rigid and non-elastic structure. Namely it is not aspired that the actuator has an elastic or damping property.

Also, a bar 15 can extend along the axis A—what is not depicted—which rests on the base part 7 and forms a bearing for the support element 6.

The hydraulic chambers 8, 9 comprise two chamber parts 8' and 9' extending in the direction of the axis A which run equally distanced from the axis A (see FIG. 3).

The two hydraulic chambers 8, 9 are connected to another by a conduit 10. A valve 11 is arranged in the conduit 10. The valve is preferably a proportional valve.

The valve 11 is supplied with actuating signals from the control device and closed-loop control device respectively 14 what is not shown in detail in the figures.

The control device and closed-loop control device respectively 14 decides in dependency on the values detected by the sensor 12 if and in which manner the actuator 3 is influenced to influence the pronation behaviour of the shoe and of the foot of the wearer of the same respectively. The possible modes of operation which result from respective actuation signals of the control device and closed-loop control device respectively 14 are shown in FIGS. 4a to 4c—however depicted in an exaggerated manner.

In FIG. 4a it can be seen that not influence of the actuator 3 is provided. Accordingly, the panel-shaped support element 6 is arranged parallel to the also panel-shaped base part 7. Consequently, the two hydraulic chambers 8, 9 are filled with the same amount of hydraulic oil. This can also not be changed because the valve 11 is kept closed. In this connection it should be mentioned however that it is not mandatory that the two chambers 8, 9 have the same size. Primary, the height of the chambers is relevant; the volume of the chambers 8, 9 can be different. The heights and the volumes of the chambers 8, 9 result finally from the geometry of the sole.

In FIG. 4a it is indicated with broken lines that a bar 15 can be arranged between the base part 7 and the support part 6 extending in the direction of the axis A which forms a bearing for the support element 6.

However, if an influencing of the foot of the wearer should occur to change the pronation the valve 11 is opened by the control device and closed-loop control device respectively 14 so that a flow of hydraulic oil from one of the hydraulic chamber 8, 9 into the other can take place.

In FIG. 4b is can be seen that a flow took place from the hydraulic chamber 9 into the hydraulic chamber 8 so that the support element 6 has tilted relatively to the base part 7, i.e. it was pivoted around the axis A.

It is important that this pivoting took place only by the opening of the valve 11 at the right time when the foot of the wearer pressed onto the support element 6. It is possible for the control device and closed-loop control device respectively 14 to determine this time because it receives the respective signals from the sensor 12 and thus "knows" when an impact onto the support element 6 takes place in that manner so that after opening of the valve 11 the desired flow of hydraulic fluid from the hydraulic chamber 9 into the hydraulic chamber 8 occurs. This flow takes place in any case in the phase of ground contact.

The opposite case is shown in FIG. 4c. Here, hydraulic fluid was allowed to flow from the hydraulic chamber 8 into the hydraulic chamber 9 analogous to the above described manner.

Thus, with the actuator 3 it can be reached that the angle position of the contact surface 4 of the sole for the foot of the wearer relatively to the contact surface 5 on the ground is changed. So, the pronation behaviour can be specifically influenced.

REFERENCE NUMERALS

1 Shoe upper
2 Sole
3 Actuator
4 Contact surface for the foot
5 Contact surface on the ground
6 Support element
7 Base part
8 Hydraulic chamber
8' Chamber part
9 Hydraulic chamber
9' Chamber part
10 Conduit
11 Valve
12 Sensor
13 Energy source (battery)
14 Control device and closed-loop control device respectively
15 Bar
L Longitudinal axis
A Axis
$B_L$ Length range
$B_B$ Width range

The invention claimed is:

1. A shoe, comprising a shoe upper and a sole, wherein at least one actuator is arranged in the sole, by means of which a region of the contact surface for the foot of the wearer of the shoe can be affected with regard to the geometry of the contact surface at least in a defined length range and/or width range of the sole relatively to the position of the contact surface of the sole on the ground,
wherein
the actuator comprises a support element supporting the foot of the wearer, which is pivotally disposed relatively to a base part around an axis, wherein at least one hydraulic chamber having a variable volume is arranged on each side of the axis between the support element and the base part, which are completely filled with a substantially incompressible medium, wherein the at least two hydraulic chambers are fluidically connected to each other by means of a conduit in which a switchable valve is disposed.

2. The shoe according to claim 1, wherein the actuator is arranged in the shoe in such a manner that the axis coincides with the longitudinal axis of the shoe.

3. The shoe according to claim 1, wherein the actuator is arranged in the rear foot region of the sole.

4. The shoe according to claim 3, wherein the actuator is arranged in the rearmost third of the extension of the sole in the direction of the longitudinal axis of the shoe.

5. The shoe according to claim 1, wherein the actuator extends along at least 80% of the width of the sole.

6. The shoe according to claim 1, wherein the support element is formed as a panel.

7. The shoe according to claim 1, wherein the base part is formed as a panel.

8. The shoe according to claim 1, wherein a bar is arranged between the base part and the support element extending in the direction of the axis which acts as a tilting joint.

9. The shoe according to claim 1, wherein the hydraulic chambers comprise an elongated chamber part which extends offset to the axis in the direction of the axis.

10. The shoe according to claim 1, wherein the hydraulic chambers are filled with hydraulic oil.

11. The shoe according to claim 1, wherein the actuator is devoid of any actuating element provided by an energy source.

12. The shoe according to claim 1, further comprising a system which comprises the at least one actuator for automatically influencing the pronation of the foot of the wearer of the shoe.

13. The shoe according to claim 12, wherein the system for automatically influencing the pronation comprises a suitable sensor for detecting of a parameter which is relevant for the pronation, an energy source and a control device and closed-loop control device respectively.

14. The shoe according to claim 13 wherein the valve can be actuated by the control device and closed-loop control device respectively.

15. The shoe according to claim 1, wherein the valve is a proportional valve.

16. The shoe according to claim 1, wherein the valve is a 2-way valve.

* * * * *